United States Patent [19]
Zutler

[11] Patent Number: 5,388,714
[45] Date of Patent: * Feb. 14, 1995

[54] CONTAINER

[75] Inventor: Michael B. Zutler, Woodbury, N.Y.

[73] Assignee: Marketing Congress, Inc., Plainview, N.Y.

[ * ] Notice: The portion of the term of this patent subsequent to Nov. 30, 2010 has been disclaimed.

[21] Appl. No.: 158,902

[22] Filed: Nov. 29, 1993

Related U.S. Application Data

[63] Continuation-in-part of Ser. No. 41,505, Apr. 1, 1993, Pat. No. 5,265,749.

[51] Int. Cl.$^6$ .............................................. B65D 83/00
[52] U.S. Cl. .................................. 220/4.24; 220/4.25; 220/360; 220/DIG. 27; 239/58
[58] Field of Search ...................... 220/4.24, 4.25, 360, 220/366, DIG. 27; 239/58, 59

[56] References Cited

U.S. PATENT DOCUMENTS

| | | | |
|---|---|---|---|
| 1,638,227 | 8/1927 | Witchger | 220/4.24 |
| 3,032,228 | 5/1962 | Andrews | 220/4.24 |
| 4,049,357 | 9/1977 | Hamisch, Jr. | 220/4.24 |
| 5,265,749 | 11/1993 | Zutler | 220/4.24 |

Primary Examiner—Joseph M. Moy
Attorney, Agent, or Firm—Grimes & Battersby

[57] ABSTRACT

A container wherein a top member and a base member are formed as identical units, e.g., from a common mold, and have interactive shapes that permit the top to be laid upon the bottom in a nesting, closed configuration, and rotated relative to the bottom to at least one open configuration with at least three pinpoints of engagement to allow for positive seating of the top member on the bottom in the open configuration and movement of ambient air therebetween. The top cover and base are divided into sections about their circumferential length. The number of sections is determined by the shape of each of the various sections. There can be any number of sections where each section is constructed so as to be able to mate with an exact inverted mirror image of itself. For each first section not so constructed, i.e., that is "irregular" and will not mate with an inverted mirror image of itself, there is a mating second section, whereby the first section on the top member can be matingly engaged with the second section tun the bottom member to effect the closed configuration. Thus, there can be any even number of such paired, mating "irregular" first and second sections. The top and bottom members can be subsequently modified, e.g., decorative or ornamental components can be added to the other, non-interfacing areas. Additionally, a handle could be added to the top cover. A pedestal could be added to the base.

9 Claims, 5 Drawing Sheets

CONTAINER

CROSS-REFERENCE TO RELATED APPLICATION

This invention is a continuation-in-part of the invention disclosed in my copending U.S. patent application Ser. No. 08/041,505, filed Apr. 1, 1993, which is scheduled to issue as U.S. Pat. No. 5,265,749, on Nov. 30, 1993.

BACKGROUND OF THE INVENTION

1. Field of the Invention

The present invention relates to a container wherein a top member and a base member are formed as identical units, e.g., from a common mold, and have interactive shapes that permit the top to be laid upon the bottom in a nesting, closed configuration, and rotated relative to the bottom to an open configuration with openings therebetween to allow for passage of ambient air.

The top cover and base, formed with identical common interfacing areas, can be subsequently modified, e.g., decorative or ornamental components can be added to the other, non-interfacing areas. Additionally, a handle could be added to the top cover. A pedestal could be added to the base.

In the preferred embodiment, each member has a curvilinear outer periphery. The top member and the base member are designed to be nested relative to each other in either a closed, first position or one or more open, second positions. When they are in one of the open, second positions, spaces are formed between the top member and the base member, which spaces are designed to permit air-treating material in the container to be exposed to ambient air. To move the members from the closed to one of the open positions, the top member is rotated relative to the base member. During such rotation, there is a concomitant upward or vertical motion of the top member away from the base member caused by the camming interaction of the interfacing outer periphery curvilinear portions of the top and base members. The members are returned to the closed position by continuing further rotation of the top member relative to the base member in the same direction that brought about the opening, or by reversing the rotation of the top member relative to the base member until the members return to their original position of closed engagement. The camming outer periphery surfaces allow easy repositioning of the top member in nesting relation to the base member even after the top member has been completely removed, e.g., in order to permit replenishment of the air-treating material. As the two members are returned to nesting engagement, the outer peripheries will engage and guide further relative movement of the two members, i.e., movement of the top member vertically downward onto the base member, until the members seat relative to each other. The nature of the interaction of the outer peripheries when the top member is being replaced on the base member is such that only two degrees (i.e., "x" and "y" planes but not "z") of rotational freedom under such circumstances is permitted, thus limiting the chances of destructive banging of the members together.

2. Description of the Prior Art

A number of container designs have been developed whereby the contents of the container may be sealed off from the ambient air and thereafter opened to expose the contents to the ambient air. The contents of the containers are air treating materials which include volatile air treating components that are gradually introduced into the air such as air freshening, air deodorizing, air purifying, perfume, disinfection and insecticidal components. Typical prior art container designs are disclosed in U.S. Pat. Nos. 4,014,501; 4,372,490; 4,537,351; 4,382,548; 4,549,693; 4,621,768; 216,831; 3,208,620; 3,983,658; 4,049,357; and 3,565,146.

Many prior art devices disclose containers whereby a top member is rotatably positioned on a bottom member. By rotating the top member relative to the bottom member either one or a plurality of apertures are opened thereby exposing the contents of the container to the ambient air. Although these devices overcome some of the deficiencies of the prior art containers, they suffer from a construction disadvantage in that the top member has a different configuration from the base member. In other words, to construct the container, it is necessary to mold the top member in a completely distinct mold from that used to mold the bottom member. This greatly increases the expense involved with constructing the container. In addition, it is necessary to closely monitor the construction of the top members and the base members to make sure that an equal quantity of members are being manufactured and to insure that manufacturing tolerances are accurate so that two different top and bottom members interact appropriately without problems.

Some prior art devices are also unsatisfactory because they require two hands to operate, i.e., to make adjustments. Others are unsatisfactory because they require a period of learning to use. Others do not permit easy replenishment of the air treatment material. Others, because of various mechanical requirements, impose design limitations which are not conducive to product aesthetics.

The LeCaire, Jr. et al. U.S. Pat. No. 4,372,490 discloses a container wherein the base and top members are matching pieces made from a common mold. However, the nesting features are complex and do not simply and effectively accomplish the goals of allowing multiple stages of opening and controlled relative movement, including during complete disengagement and reengagement of the two members. Neither does this design result in an acceptable container from an aesthetic standpoint nor permit removal of the top for replenishment of the material in the container. Nor does this design accomplish closed and open engagement controlled by the specially designed interfacing outer periphery portions of the top and base members.

SUMMARY OF THE INVENTION

Accordingly, it is a primary object of the present invention to provide a container wherein the top member and the base member are identical elements constructed from a single mold.

Another object of the present invention is to provide a container formed with identical interfacing areas that may have different design or aesthetic areas beyond the interface areas.

Another object of the present invention is to provide a container wherein the top member and the base member may be nested together in order to form an operative container which may be closed or opened.

A still further object of the present invention is to provide a container which is simple in construction and operation and at the same time attractive in appearance.

A further object of the present invention is to provide a top member and a base member which include outwardly projecting outer peripheries which mate with each other so that the top member may be reciprocated outwardly from the base member thereby defining air passages therebetween and inwardly to close and seal the container.

A still further object of the present invention is to provide a container wherein a top member and a base member are formed as identical units, e.g., from a common mold, and have interactive shapes that permit the top to be laid upon the bottom in a nesting, closed configuration, and rotated relative to the bottom to one or more open configurations with at least three pinpoints of engagement whereby the size of the openings therebetween are varied in the different open positions.

A still further object of this invention is to provide a container which can have any desired number of periphery shapes.

A still further object of the invention is to provide outer peripheries which can be curvilinear in shape so as to permit smooth rotation of the two members relative to each other and indexing of the two peripheries relative to each other to adjust the positioning of said top member relative to said base member in a plurality of various positions to define different size air passages.

An additional object of the invention is to provide outer peripheries which are scalloped shaped in design so as to achieve the desired smooth rotation and indexing in an extremely, aesthetically attractive container.

An additional object is to provide a design that permits any number of sections along the outer peripheries, thus permitting any number of periphery shapes, ranging from single squares, pentagons and hexagons to multiple sided shapes with unlimited numbers of sections and sides.

These and other objects have been fulfilled in the present invention by providing a top member which is constructed in an identical configuration to the base member. The top member and base member each include an outer periphery that matingly engages the outer periphery of the other in a closed position and in one or more open positions. In the closed position, the outer peripheries are in complete engagement along their entire length. In the open positions, the outer peripheries are only in engagement along certain select portions of their length, in particular, along at least three distinct pinpoints of their lengths, and interspersed between those engaging portions are other non-engaging portions, which define air passages therebetween. A quantity of air-treating material is positioned between the top member and the base member and is normally positioned within the base member. In the open position, the top member is rotated relative to the base member to shift the top member upwardly away from the base member. The outer peripheries are divided into multiple sections. The number of different sections is dependent upon the number of regular sections and the number of irregular sections around the periphery of the top and bottom members. A regular section is a section capable of mating engagement with an inverted mirror image of itself. An irregular section is incapable of mating with an inverted mirror image of itself and can only mate with a second irregular section. There can be any multiple of regular sections. There must be mating pairs of irregular sections. The outer peripheries can be curvilinear in shape, in which case such upward movement upon rotation of the top member is due to the camming interaction between the outer peripheries.

BRIEF DESCRIPTION OF THE DRAWINGS

The objects of the present invention and the attendant advantages thereof will become more readily apparent by reference to the following drawings wherein.

DETAILED DESCRIPTION OF THE PREFERRED EMBODIMENTS

Figure 1:
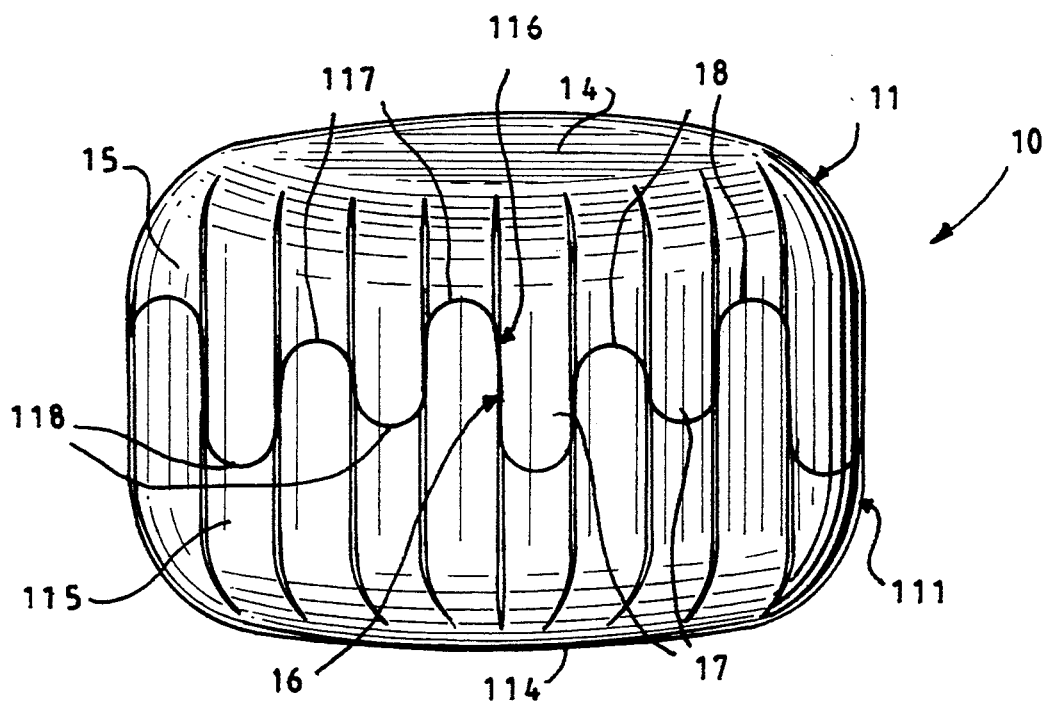
FIG. 1 is a side perspective view illustrating a preferred embodiment of the container according to the present invention in a closed position.
Figure 2:
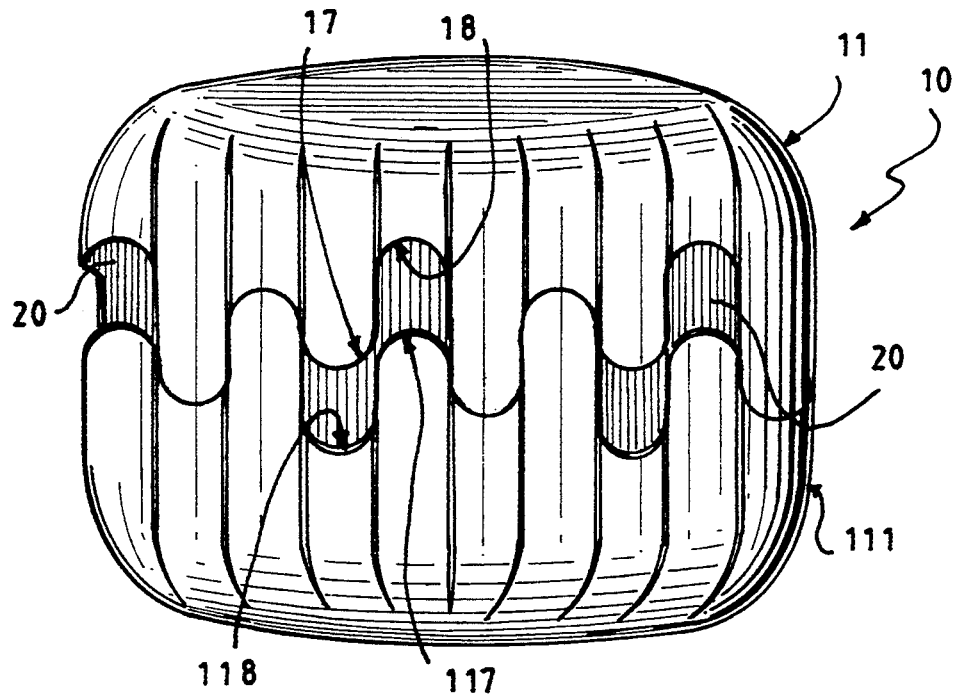
FIG. 2 is a side perspective view of the container according to the present invention illustrating the container in an open position.
Figure 3:
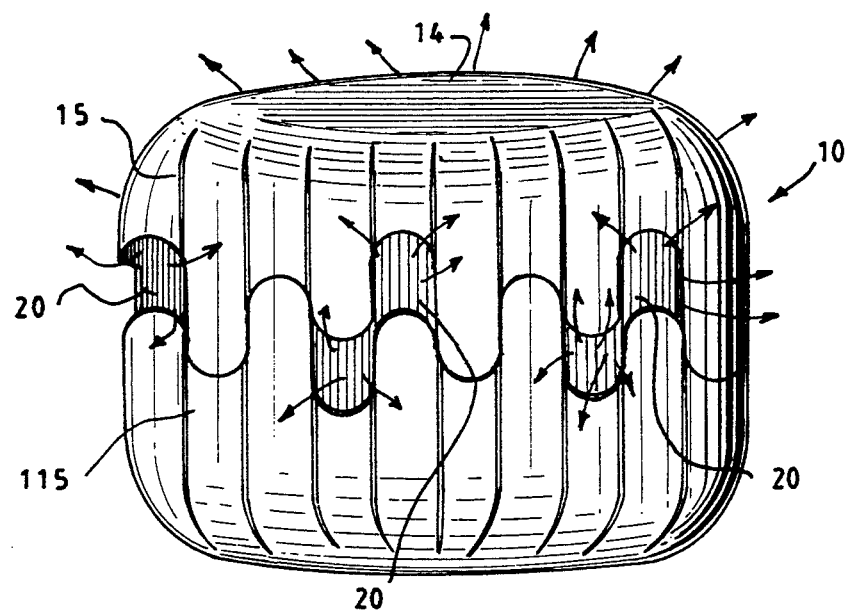
FIG. 3 is a side perspective view of the container according to the present invention illustrating the passage of ambient air through the container in an open position.
Figure 4:
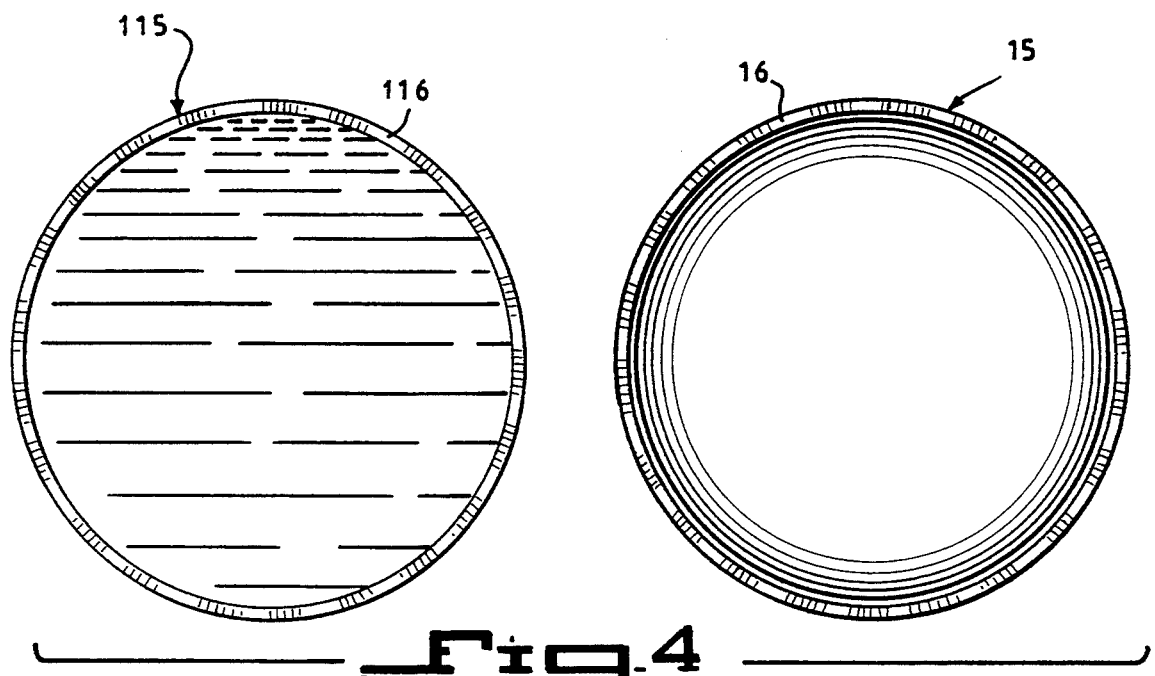
FIG. 4 is a top plan view of the top and base members of the container according to the present invention, disengaged from each other and laid side by side with their outer peripheries extending up out of the plane of the paper.
Figure 5:
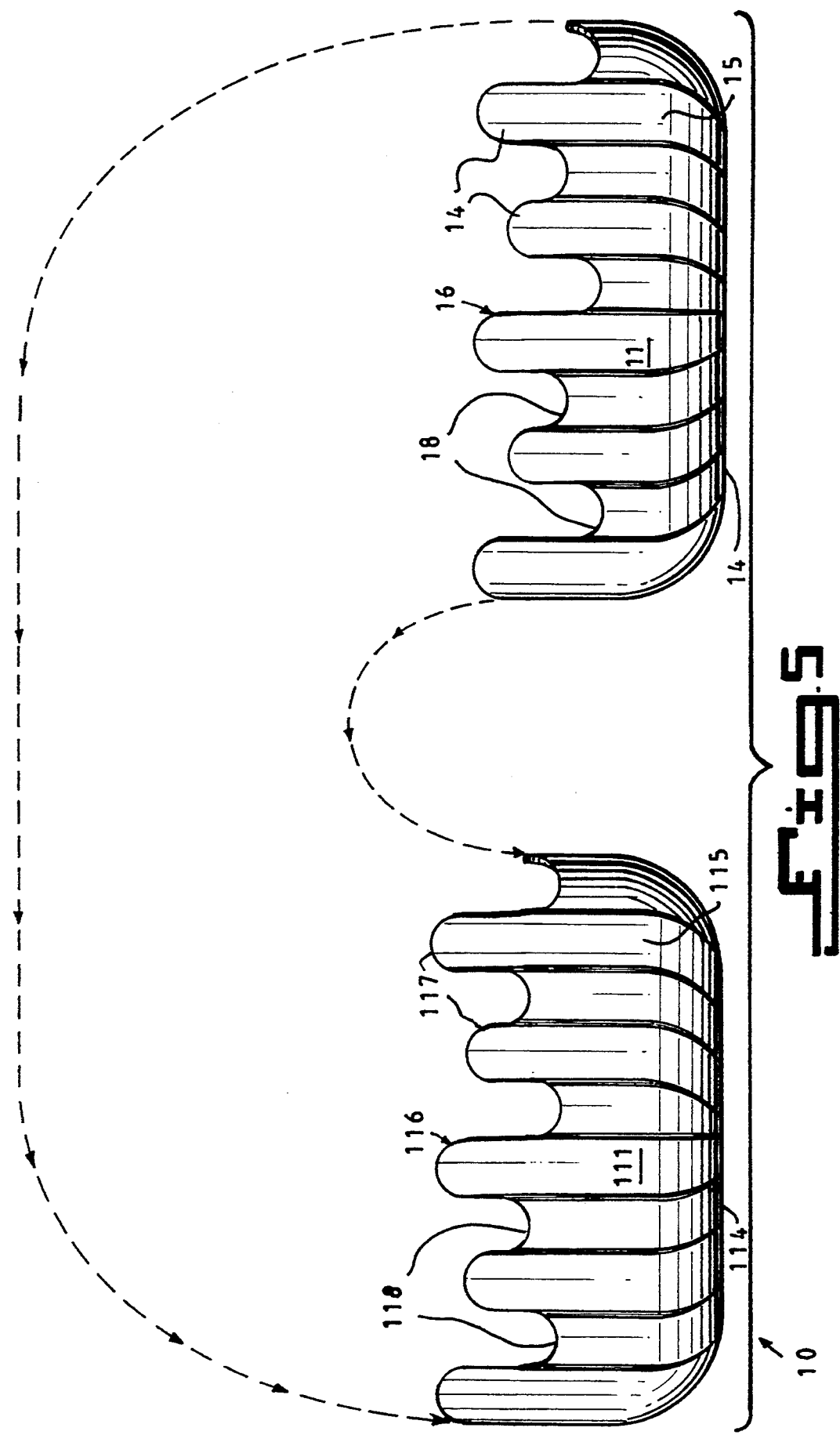
FIG. 5 is a side view of the top and base members of the container according to the present invention, disengaged from each other and laid side by side.
Figure 6:
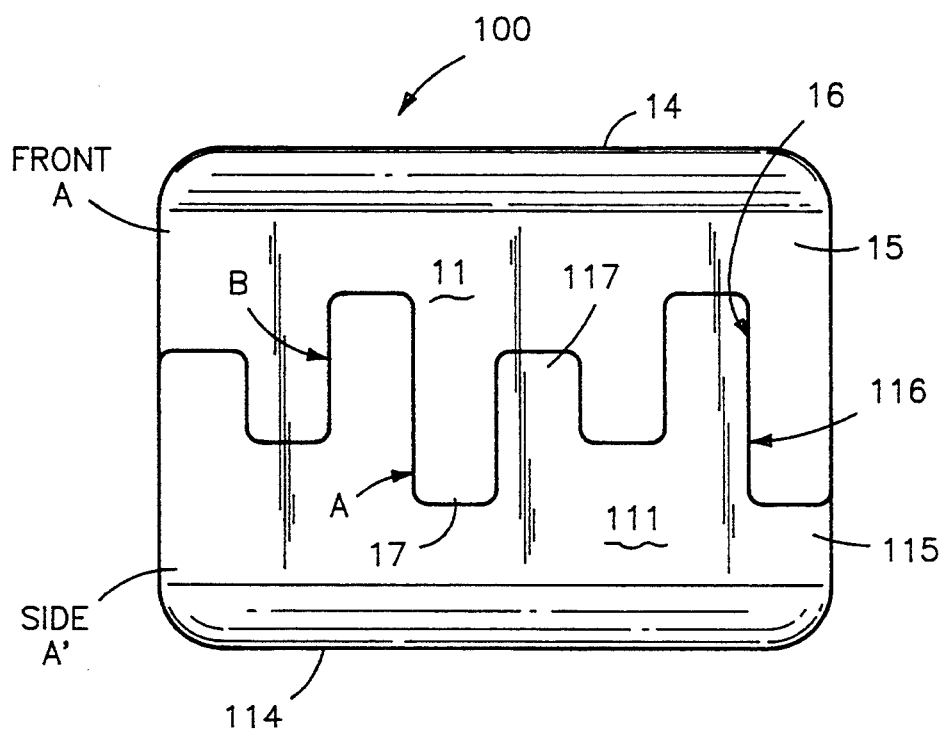
FIG. 6 is a side view of an alternate four-sided embodiment of the container according to the present invention in a closed position, showing a section one of the top labeled "Front A" on a section two of the bottom labeled "Side A'".

Referring in detail to FIG. 1, there is illustrated a container 10 shown in the closed position. The container 10 includes a top member or housing section 11 which is identical in construction to a base member or housing section 111, i.e., the top member 11 and the base member 111 have the identical shape, having been made from the same mold. The top member 11 includes a flat upper surface 14 and a side wall 15. The side wall 15 includes a curvilinear outer periphery or edge 16 that, in the preferred embodiment shown, is scallop shaped. The periphery 16 is defined by fingers 17 and recesses 18 which are, at the same time, both functional and decorative.

Similarly, the base member 111 includes a flat lower surface 114 and a side wall 115 which includes a curvilinear outer periphery or edge 116 that, in the preferred embodiment shown, is scallop shaped. The periphery 116 is defined by fingers 117 and recesses 118 that correspond respectively with the fingers 17 and recesses 18 of the top member 11.

The fingers 17 and 117 are designed to mate with each of the recesses 118 and 18, respectively.

As shown in FIG. 1, the outer periphery 16 of the top member 11 engages the outer periphery 116 of the base member 111 when the container is in the first, closed position to close the interior of the container form the outside air. As discussed hereinbelow, the embodiment of the container 10 shown has a curvilinear shape whereby it repeats after every two fingers and two recesses, although it is possible to have repeats after three or more fingers and recesses.

In the alternate embodiment shown in FIGS. 6–9, the container is four-sided. Elements in the alternate embodiment that are common to the elements in the preferred embodiment described hereinabove are similarly numbered in the alternate embodiment.

Figure 7:
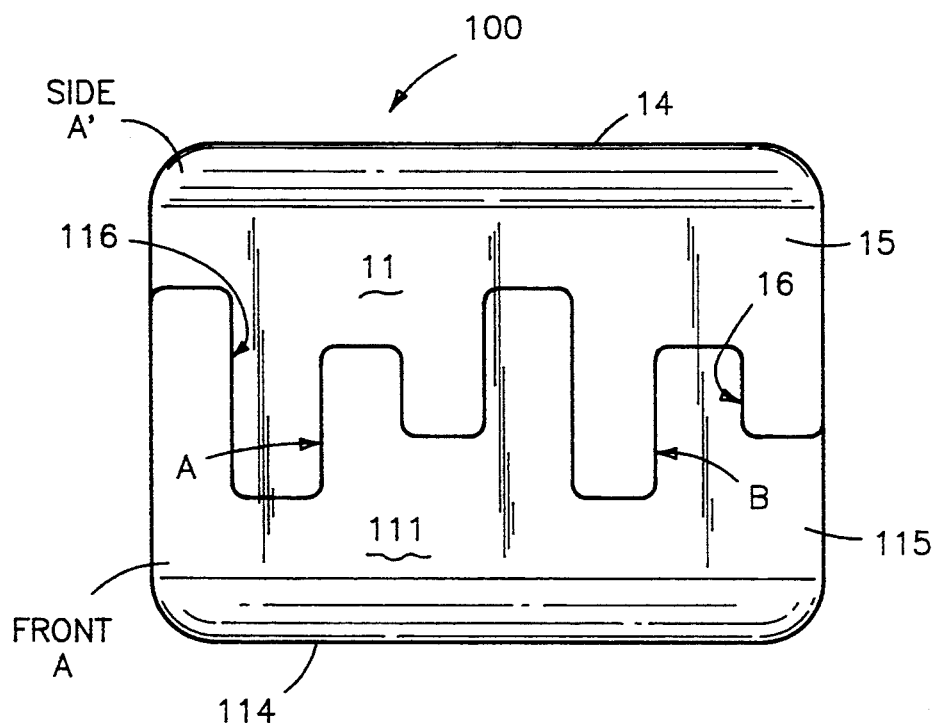
FIG. 7 is a side view of the alternate four-sided embodiment of the container according to the present invention in a closed position, showing the corresponding section two of the top also labeled "Side A'" on the corresponding section one of the bottom labeled "Front A".

The outer peripheries 16 and 116 of the top and bottom members of the alternate embodiment include irregular sections. The section Front A of the periphery 16 shown in FIG. 6, namely, the section of the periphery 16 that extends across the first side of the top member shown in FIG. 6, would not matingly engage in a closed position with a section of the periphery 116 on the bottom member that is an identical, inverted mirror image of section FRONT A. Thus, a mating section SIDE A' is provided in the periphery 116 of the bottom section of the first side of the bottom member shown in FIG. 6 that matingly engages section FRONT A of periphery 16 of the top in the closed position shown in FIG. 6. Inasmuch as the top and bottom members are constructed to be identical, section FRONT A must thus also exist in the periphery of the bottom and likewise section SIDE A' must thus also exist in the periphery of the top. Thus, FIG. 7 shows the periphery 16 of the top with a section SIDE A' and the periphery 116 of the bottom with a mating section FRONT A.

Figure 8:
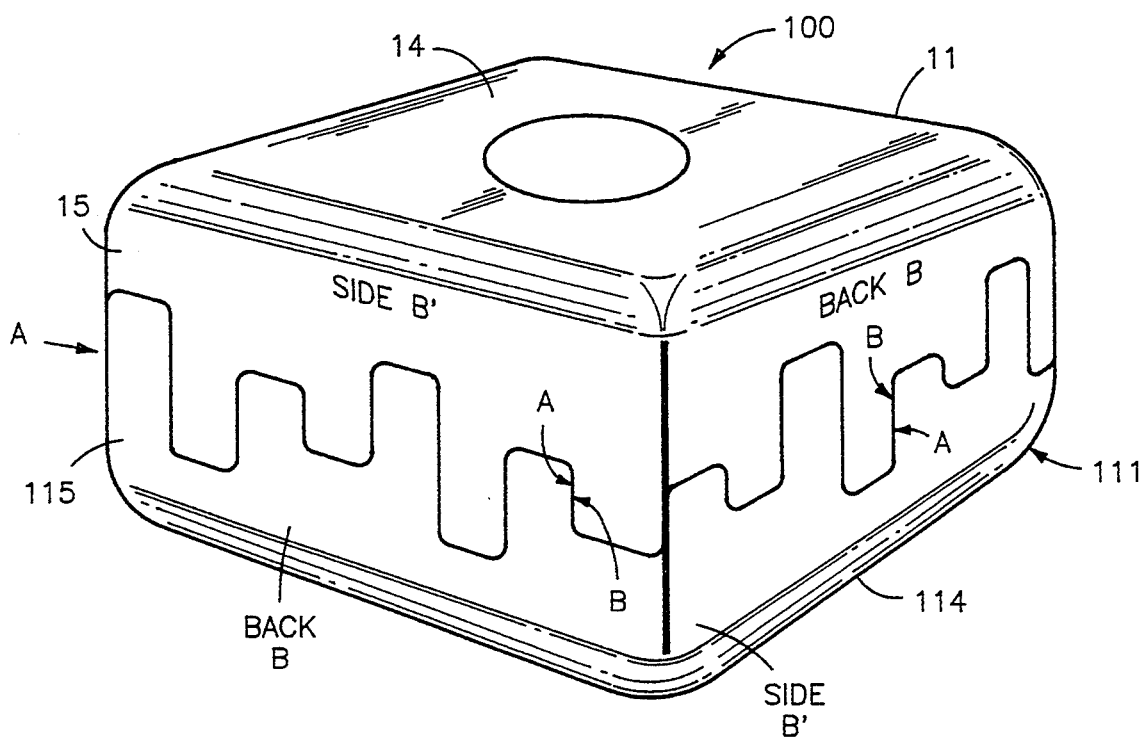
FIG. 8 is a perspective view of the alternate four-sided embodiment of the container according to the present invention in a closed position, showing the other two sides of the container not seen in FIGS. 6 and 7.
Figure 9:
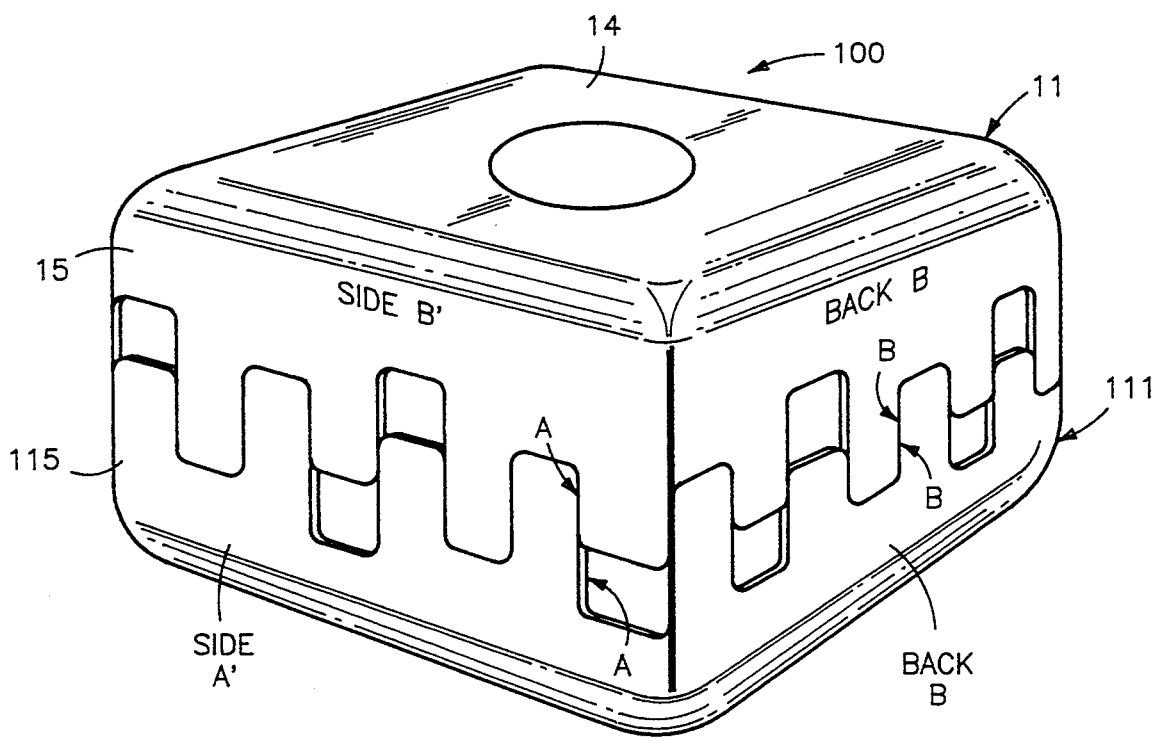
FIG. 9 is a perspective view from the lefthand side of FIG. 8 looking in the direction of arrow A of the alternate four-sided embodiment of the container according to the present invention in an open position, showing the top having been rotated 90° in a clockwise direction relative to the bottom.

FIG. 8 clearly shows the sections SIDE B' and BACK B on the top member 11 and identical sections BACK B and SIDE B' on the bottom member 111. In the alternate embodiment shown, the third side BACK B of the top and bottom is identical to the first side FRONT A and the fourth side SIDE B' of each is identical to the second side SIDE A'. The third and fourth sides (BACK B and SIDE B') could, however, have been different (i.e., not identical respectively to FRONT A and SIDE A'), so long as the section of the periphery of side three (BACK B) of the top was a mate for sealing engagement with the section of the periphery of side four (SIDE B') of the bottom and the section of the periphery of side four (SIDE B') of the top was a mate for sealing engagement with the section of the periphery of side three (BACK B) of the bottom.

The alternate embodiment shows the use of identical width, albeit different length, fingers 17 and 117, and identical width, albeit different depth, recesses 18 and 118, along the periphery of both the top and bottom members, which fingers and recesses permit the positive seating engagement of the top and bottom members in both closed and open positions.

In other versions of the alternative embodiment, there could be repetitive sequences of fingers and recesses, accomplished by inserting fingers in between the two fingers shown of varying progressive sizes between the size of the smaller finger and the size of the larger finger and by inserting matching recesses in between the two recesses shown of varying progressive depths between the depth of the smaller recess and the depth of the larger recess. This would afford additional opened positions which the container can be rotated to in order to selectively control the release of the air treatment material. The greater the number of fingers and recesses, the greater the number of possible opened positions. Adding additional numbers of fingers and recesses permits more refined selection of the degree of material being released into the air.

Also in alternative embodiments, there could be containers with varying numbers of sides. Besides the one continuous circular sided embodiment shown in FIGS. 1–5 and the four-sided embodiment shown in FIGS. 6–9, there could be two, three, five, six or more sided containers. There must simply be any number of regular sections and an even number of irregular sections that are thus paired for mating closed engagement. The sections should be able to seat with varying other sections. This can be accomplished in numerous ways; for example, in a three sided container having on sides one and two peripheries with sections identical to the sections FRONT A and SIDE A′ of the sides shown in the alternate embodiment, the third side could be a regular side having only two fingers and two recesses that are respectively double the width of the fingers 17 and 117 and the recesses 18 and 118.

Referring in detail to FIG. 2, the container 10 is illustrated in the open position. Like numerals in FIG. 2 represent the same elements as previously discussed with respect to FIG.1. In the open position shown, the total sealing engagement of 16 and 116 has been discontinued. shown, the total sealing engagement of 16 and 116 has been discontinued. As a result of rotational motion of the top member 11 relative to the base member 111, a plurality of spaced portions 20 have been created between the top member 11 and the base member 111.

Referring in detail to FIG. 3, the container 10 is illustrated in the open position. Once again, like numerals in FIG. 3 represent the same elements as previously discussed with respect to FIGS. 1 and 2. In the open position shown, ambient air circulates through the container in the manner indicated by the arrows.

Referring in detail to FIGS. 4 and 5, in each case the container is shown with the two components taken apart and laid side by side, i.e., the base member on the left and the top member on the right. Since the periphery of the top member is curvilinear, there correctly is no indication in FIG. 4 as to where the curvilinear portions change direction or even where the changeovers back and forth from the fingers to the recesses and vice versa takes place.

The manner in which the top member is picked up and seated on the base member is illustrated in dotted lines in FIG. 5 and the figure also shows how the two halves can be put together and separated.

In operation, the container is originally closed whereby the fingers and recesses of the outer peripheries of the top and base members engage each other and form a sealing engagement of the top and base members.

If one desires to open the container 10, one merely rotates the top member 11 relative to the base member 111. Such rotation causes reciprocation of the top member 11 relative to the base member 111, due to the camming interaction of the outer peripheries of top member 11 and base member 111. When the top member reciprocates away from the bottom member, the container is opened providing air passages 20 between the top member 11 and the base member 111. In the open condition, the container is activated to treat the air within the room in which it is positioned.

The outer peripheries interact to cause the top member to securely rest on the base member in a nesting configuration. Depending upon the alignment, the top member can rest on the base member in the closed, partial open or full open position. No matter how the top member is initially aligned with the base member, the top member will always rest securely on the base member because once the top member is positioned on the base member, the top member will slide downwardly onto the base member until the two members nest together. It is not possible for the top member to lean, i.e., rotate about any axis in a plane parallel to the plane of the section's upper (or in the case of the base, its lower) surface. The top section cannot slip off or strike the bottom section when being re-engaged. At most, the top member will slide down onto the base member, possibly twisting relative to the base member, but with the top and base upper and lower surfaces respectively always remaining parallel.

The outer peripheries of the top and base sections can be curvilinear to avoid sharp edges and to reduce the possibility of breakage of such sharp edges, and to achieve the desired nesting and camming interaction.

The invention being thus described, it would be obvious that the same may be varied in many ways. By way of example, in the most simplified version of the invention, the camming aspects could be left out and the interfacing surfaces could be squared off or step-like configurations. The members would be moved relative to each other by lifting the top member entirely off the bottom member and rotating the top member relative to the bottom member and then repositioning the top member on the bottom member. Such variations are not to be regarded as a departure from the spirit and scope of the invention, and all such modifications as would be obvious to one skilled in the art are intended to be included within the scope of the following claims.

What is claimed is:

1. A container for an air treatment material, said container having first and second top and bottom housing sections, said housing sections each having an outer peripheral edge that is identical to and interacts with the outer peripheral edge of the other and permits the top to be laid upon the bottom in a nesting, closed configuration with the outer peripheries in engagement along their entire lengths, and the top to be moved to a different position of engagement relative to the bottom to one or more open configurations, said outer peripheries having selected portions of their lengths which are in engagement with each other in said open positions and selected other portions of their lengths which are not in engagement with each other, but rather, spaced apart from each other, in said open positions, said other nonengaging, spaced apart portions of said outer peripheries defining air passages therebetween, said air passages extending into the interior of said container and said air passages being closed when the container is in the closed position, said peripheries of said housing sections having any number of regular sections and an even number of paired irregular sections.

2. A container according to claim 1, wherein said outer peripheries engage along at least three pinpoints of engagement in each of said open positions.

3. A container according to claim 1, wherein said irregular sections of said outer peripheries are paired, mating shapes on the top and bottom housing sections.

4. A container according to claim 1, whereby the size of the openings between the housing sections are varied in the different open positions.

5. A container according to claim 1, wherein said outer peripheries have varying numbers of regular and irregular sections and concomitant varying number of sides.

6. A container according to claim 1, wherein said top member and said base member are identical elements constructed from a single mold.

7. A container according to claim 1, wherein said top member and said base member include outwardly projecting outer peripheries which mate with each other so that the top member may be reciprocated outwardly from the base member thereby defining air passages therebetween and inwardly to close and seal the container.

8. A container according to claim 1, wherein said outer peripheries are any irregular shape.

9. A container according to claim 1, wherein different sides of the top and bottom housing sections can be matingly engaged with each other.

* * * * *